(12) United States Patent
Nicolas-Morgantini et al.

(10) Patent No.: US 7,608,116 B2
(45) Date of Patent: Oct. 27, 2009

(54) OXIDATION DYE COMPOSITION COMPRISING AT LEAST ONE MESOMORPHIC PHASE, PROCESS FOR PREPARING IT AND READY-TO-USE COMPOSITION FOR DYEING KERATIN MATERIALS

(75) Inventors: Luc Nicolas-Morgantini, Rully (FR); Jean-Marc Petit, Clichy (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/743,004

(22) Filed: Dec. 23, 2003

(65) Prior Publication Data

US 2004/0194230 A1    Oct. 7, 2004

Related U.S. Application Data

(60) Provisional application No. 60/469,407, filed on May 12, 2003.

(30) Foreign Application Priority Data

Dec. 24, 2002    (FR)    .................................... 02 16599

(51) Int. Cl.
*A61Q 5/10* (2006.01)
(52) U.S. Cl. ...................... 8/405; 8/406; 8/408; 8/409; 8/410; 8/411; 8/412; 8/421; 8/435; 8/611; 8/619
(58) Field of Classification Search ...................... 8/405, 8/406, 408, 409, 410, 411, 412, 421, 435, 8/611, 619
See application file for complete search history.

(56) References Cited

U.S. PATENT DOCUMENTS

| | | | |
|---|---|---|---|
| 3,768,490 A | 10/1973 | Kalopissis et al. | |
| 3,975,515 A | 8/1976 | Wajaroff et al. | |
| 4,366,827 A | 1/1983 | Madrange et al. | |
| 4,394,520 A | 7/1983 | Kalopissis | |
| 4,533,714 A | 8/1985 | Sebag et al. | |
| 4,548,811 A | 10/1985 | Kubo et al. | |
| 4,560,554 A | 12/1985 | Kubo et al. | |
| 4,587,321 A | 5/1986 | Sebag et al. | |
| 4,749,732 A | 6/1988 | Kohl et al. | |
| 4,781,724 A | 11/1988 | Wajaroff et al. | |
| 4,880,618 A | 11/1989 | Grollier et al. | |
| 4,956,175 A | 9/1990 | Maignan et al. | |
| 4,996,059 A | 2/1991 | Grollier et al. | |
| 5,015,767 A | 5/1991 | Maignan et al. | |
| 5,021,200 A * | 6/1991 | Vanlerberghe et al. ....... 264/4.3 | |
| 5,085,860 A | 2/1992 | Junino et al. | |
| 5,106,612 A | 4/1992 | Maignan et al. | |
| 5,334,377 A | 8/1994 | Junino et al. | |
| 5,449,805 A | 9/1995 | Junino et al. | |
| 5,466,878 A | 11/1995 | Junino et al. | |
| 5,583,257 A | 12/1996 | Junino et al. | |
| 5,958,392 A | 9/1999 | Grollier et al. | |
| 6,572,663 B1 | 6/2003 | Pitfield et al. ................... | 8/405 |
| 6,173,717 B1 | 2/2004 | Legrand et al. | |
| 6,871,652 B1 | 3/2005 | Mueller et al. | |
| 6,991,781 B2 | 1/2006 | Glenn, Jr. et al. | |
| 2001/0023514 A1 * | 9/2001 | Cottard et al. ................... | 8/406 |
| 2004/0034946 A1 | 2/2004 | Legrand et al. | |
| 2005/0042190 A1 | 2/2005 | Nicolas-Morgantini et al. | |

FOREIGN PATENT DOCUMENTS

| | | |
|---|---|---|
| DE | 40 05 008 | 8/1991 |
| EP | 0 295 780 | 12/1988 |
| EP | 0 312 343 | 4/1989 |
| EP | 0 354 835 | 2/1990 |
| EP | 0 368 763 | 5/1990 |
| EP | 0 432 000 | 6/1991 |
| EP | 0 514 282 | 11/1992 |
| FR | 1 313 557 | 11/1962 |
| FR | 1 530 369 | 6/1968 |
| FR | 2 470 596 | 6/1981 |
| FR | 2 472 382 | 7/1981 |
| FR | 2 495 931 | 6/1982 |
| FR | 2 535 730 | 5/1984 |
| FR | 2 598 613 | 11/1987 |
| FR | 2 679 448 | 1/1993 |
| FR | 2 816 210 | 5/2002 |
| GB | 1 199 776 | 7/1970 |
| GB | 2 026 052 | 1/1980 |
| GB | 2 197 352 | 5/1998 |
| LU | 83703 | 10/1981 |
| WO | WO 97/04738 | 2/1997 |
| WO | WO 99/30676 | 6/1999 |
| WO | WO 02/41983 | 5/2002 |

OTHER PUBLICATIONS

English language Derwent Abstract of DE 40 05 008, Aug. 22, 1991.

(Continued)

*Primary Examiner*—Eisa B Elhilo
(74) *Attorney, Agent, or Firm*—Finnegan, Henderson, Farabow, Garrett & Dunner

(57) ABSTRACT

The present disclosure relates to oxidation dye compositions comprising, in an aqueous medium suitable for dyeing, at least one oxidation dye, ammonia, and at least one mesomorphic phase present in an amount greater than or equal to 10% by weight, relative to the weight of the composition. The present disclosure also relates to the process for preparing the compositions, as well as ready-to-use compositions for oxidation dyeing of keratin fibers, and multi-compartment kits for oxidation dyeing of keratin fibers, wherein at least one compartment contains the dye composition. Another aspect of the present disclosure is an oxidizing composition comprising a mesomorphic phase.

48 Claims, No Drawings

OTHER PUBLICATIONS

Office Action mailed Apr. 13, 2009, in co-pending U.S. Appl. No. 10/745,366.
Office Action mailed Jul. 7, 2008, in co-pending U.S. Appl. No. 10/745,366.
Office Action mailed Oct. 2, 2007, in co-pending U.S. Appl. No. 10/745,366.
Charvolin, J., et al., La Recherche, vol. 23, Mar. 1992, pp. 306-315.
English language Abstract of WO 97/04738, dated Feb. 13, 1997.
English language Derwent Abstract of EP 0 368 763, May 16, 1990.
English language Derwent Abstract of FR 2 679 448, Jan. 29, 1993.
English language Derwent Abstract of LU 83703, Oct. 20, 1981.
Engstrom, S., et al., Lipd Technology, vol. 2, No. 2, Apr. 1990, pp. 42-45.
French Search Report for FR 02/16599, dated Jun. 19, 2003.
Griffin, W.C., "Calculation of HLB Values of Non-Ionic Surfactants," J. Soc. Cosm. Chem. vol. 5, pp. 249-256 (1954).
Puisieux, F., et al., Galencia 5: Les Systemes Disperses, pp. 153-194, (1981).
Small, D.M., "The Physical Chemistry of Lipids from Alkanes to Phospholipids," Handbook of Lipid Research, 4, 1986, Plenum Press, pp. 51-56.

* cited by examiner

OXIDATION DYE COMPOSITION COMPRISING AT LEAST ONE MESOMORPHIC PHASE, PROCESS FOR PREPARING IT AND READY-TO-USE COMPOSITION FOR DYEING KERATIN MATERIALS

This application claims benefit of U.S. Provisional Application No. 60/469,407, filed on May 12, 2003.

The present disclosure relates to oxidation dye compositions, methods for preparing the dye compositions, ready-to-use compositions for the oxidation dyeing of keratin fibers, such as the hair, a dyeing process, oxidation compositions, and a dyeing kit.

It is known to dye keratin fibers, such as human hair, with dye compositions comprising oxidation dye precursors, generally known as "oxidation bases," for example, ortho- or para-phenylenediamines, ortho- or para-aminophenols and heterocyclic bases.

Oxidation dye precursors are compounds that are initially uncolored or only weakly colored and which can develop their dyeing power on the hair in the presence of oxidizing agents, leading to the formation of colored compounds. The formation of these coloured compounds may result from an oxidative condensation of the "oxidation bases" with themselves, or from an oxidative condensation of the "oxidation bases" with coloration modifiers, or "couplers," which may be present in the dye compositions used in oxidation dyeing and may be, for example, meta-phenylenediamines, meta-aminophenols and meta-diphenols, and certain heterocyclic compounds.

The variety of molecules used, which may be on the one hand, the "oxidation bases" and on the other hand the "couplers," can allow a wide range of shades to be obtained.

Known dye compositions may comprise ammonia as a basifying agent, and, during their application to the hair, ammonia is given off, resulting in an unpleasant odor.

The inventors have surprisingly and unexpectedly found that this release of ammonia can be greatly limited by adding at least one mesomorphic phase into a dye composition comprising at least one oxidation dye and ammonia, in an amount greater than or equal to 10% by weight relative to the total weight of the dye composition.

Substantial limitation of the release of ammonia can be obtained during the application to the keratin fibers of a ready-to-use composition comprising a dye composition as disclosed herein, whether the ammonia is contained in the mesomorphic phase or outside this mesomorphic phase.

As disclosed herein, the term "keratin fibers" means the hair, the eyelashes and the eyebrows.

Therefore, in one aspect of the present disclosure is provided a dye composition comprising, in an aqueous medium suitable for dyeing, at least one oxidation dye, ammonia, and at least one mesomorphic phase present in the dye composition in an amount greater than or equal to 10% by weight, relative to the total weight of the dye composition.

Another aspect of the present disclosure is a process for preparing the dye compositions as disclosed herein.

Yet another aspect of the present disclosure is a ready-to-use composition for dyeing keratin fibers, for example, the hair.

Still another aspect of the present disclosure is an oxidizing composition comprising at least on mesomorphic phase.

A further aspect of the present disclosure is a dyeing kit.

Other aspects, characteristics, and advantages of the present disclosure will emerge upon reading the description and the various examples that follow.

For example, as disclosed herein, the dye composition may comprise, in an aqueous medium suitable for dyeing, at least one oxidation dye, ammonia, and at least one mesomorphic phase in an amount greater than or equal to 10% by weight, for example, at least 15% by weight, relative to the total weight of the dye composition.

For instance, the dye composition may comprise the at least one mesomorphic phase in an amount ranging from 10% to 85% by weight, relative to the total weight of the dye composition.

The term "mesomorphic phase" means a state that is intermediate between a crystalline state and a liquid state. The mesomorphic phase used in the composition as disclosed herein may be chosen from, for example, inverse hexagonal phases ($H_2$), lamellar phases ($L_\alpha$ and $L_\beta$) and inverse cubic phases ($I_2$ and $V_2$). For instance, a lamellar phase $L_\beta$ may be used in the invention.

The term "inverse hexagonal phase" ($H_2$) means a hexagonal arrangement of parallel cylindrical micelles of amphiphilic molecules (Handbook of lipid research 4, the physical chemistry of lipids from alkanes to phospholipids, D. M. Small Editor, 1986, Plenum Press, pp. 51-56).

The term "fluid lamellar phase" (or phase $L_\alpha$) means a phase wherein the surfactant molecules and/or more generally the molecules of amphiphilic compounds become organized in the form of bimolecular layers separated by aqueous leaflets. Within the bimolecular layers, the molecules are distributed according to hexagonal or orthorhombic geometry and their fatty chains are in a liquid state, also they are oriented perpendicular to the plane of the bimolecular layers, but do not have any specific orientation relative to each other in the plane of these layers (Handbook of lipid research 4, the physical chemistry of lipids from alkanes to phospholipids, D. M. Small Editor, 1986, Plenum Press, pp. 51-56).

The term "fluid lamellar phase" (phase $L_\beta$) means a phase wherein the surfactant molecules and/or more generally the molecules of amphiphilic compounds become organized in the form of bimolecular layers separated by aqueous leaflets. Within the bimolecular layers, the molecules are distributed according to hexagonal or orthorhombic geometry and their hydrocarbon-based chains are in a crystalline state, also they are oriented perpendicular to the plane of the bimolecular layers, but do not have any specific orientation relative to each other in the plane of these layers (Handbook of lipid research 4, the physical chemistry of lipids from alkanes to phospholipids, D. M. Small Editor, 1986, Plenum Press, pp. 51-56).

The term "cubic phase" means a phase organized in a bipolar manner into separate hydrophilic and lipophilic domains, in close contact and forming a cubic symmetry three-dimensional network. Such an organization has been described for example, in "La Recherche", Vol. 23, pages 306-315, March 1992 and in "Lipid Technology", Vol. 2, No. 2, pages 42-45, April 1990. According to the arrangement of the hydrophilic and lipophilic domains, the cubic phase is said to be of direct or inverse type. The inverse cubic phase corresponds to an oily continuous phase.

The structure of the mesomorphic phase may be checked by polarization microscopy and small-angle X-ray scattering or any other method that it is known in the art.

According to the present disclosure, the mesomorphic phase may comprise, for example, at least one nonionic surfactant with an HLB value of less than or equal to 10, such as an HLB value ranging from 1 to 5, chosen from monooxyalkylenated and polyoxyalkylenated, monoglycerolated and polyglycerolated nonionic surfactants.

The HLB value, or hydrophilic-lipophilic balance, of the at least one nonionic surfactant as disclosed herein is the HLB value according to Griffin defined in publication J. Soc. Cosm. Chem. 1954 (Volume 5), pages 249-256, or the HLB value experimentally determined and as described in the book by the authors F. Puisieux and M. Seiller, entitled Galenica 5: Les systèmes dispersés—Tome I—Agents de surface et émulsions—Chapitre IV—Notions de HLB et de HLB critique, pages 153-194—paragraphe 1.1.2. Détermination de HLB par voie expérimentale [Galenica 5: Dispersed systems—Volume I—Surface agents and emulsions—Chapter IV, Notions of HLB and of critical HLB, pages 153-194—paragraph 1.1.2. Determination of HLB experimentally], pages 164-180.

As disclosed herein, the expression "monooxyalkylenated and polyoxyalkylenated nonionic surfactants" means nonionic surfactants comprising in their molecule at least one oxyalkylene group chosen from the following groups: —$CH_2$—$CH_2$—O—, —$CH_2$—$CH_2$—$CH_2$—O—, and —$CH_2$—$CH(CH_3)$—O—.

As disclosed herein, the expression "monoglycerolated and polyglycerolated nonionic surfactants" means nonionic surfactants comprising in their molecule at least one glycerol group.

Non-limiting examples of surfactants that may be used as disclosed herein include: polyglycerolated fatty alcohols, monooxyethylenated or polyoxyethylenated fatty alcohols, monoglycerolated or polyglycerolated fatty amides comprising on average from 1 to 5 glycerol groups, monooxyethylenated or polyoxyethylenated alkylphenols condensates of ethylene oxide and of propylene oxide onto fatty alcohols, polyoxyethylenated vegetable oils, fatty acid esters of polyethylene glycols and polyoxyethylenated fatty acid esters of sorbitol, and mixtures thereof.

As examples of nonionic surfactants with an HLB greater than 5, non-limiting mention may be made for example, of those sold under the following brand names:

IMBENTIN POA/024 (HLB=5.5) by the company ICI, SYNPERONIC PE L92 (HLB=5.5) by the company ICI, MERGITAL LM2 (HLB=5.8) by the company Henkel, ATLAS G-70140 (HLB=6) by the company ICI, IMBENTIN AG/124S/020 (HLB=6) by the company Kolb, IMBENTIN L/125/025 HLB=6 by the company Kolb, SIMULSOL 989 (HLB=6) by the company SEPPIC, SOPROPHOR HR10 (HLB=6) by the company Rhône-Poulenc, KOTILEN O/1/050 (HLB=6.2) by the company Kolb, CRODURET 10 (HLB=6.3) by the company Croda, ETOCAS 10 (HLB=6.3) by the company Croda, IMBENTIN OA/030 (HLB=6.3) by the company Kolb, SOPROPHOR 208 (HLB=6.9) by the company Rhône-Poulenc, ETHYLAN 172 (HLB=7) by the company Harcros, AKYPOROX NP 40 (HLB=7.1) by the company Chemy, POLYCHOL 5 (HLB=7.3) by the company Croda, ARLATONE 985 (HLB=7.5) by the company ICI, SANDOXYLATE FOL4 (HLB=7.5) by the company Sandoz, RADIASURF 7453 (HLB=7.8) by the company Oleofina, PROX-ONIC OA-1/04 (HLB=7.9) by the company Protex, PROX-ONIC TD-1/03 (HLB=7.9) by the company Protex, GENAPOL PF 40 (HLB=8) by the company Hoechst, PGE-400—DS (HLB=8) by the company Hefti, PGE-400—DO (HLB=8) by the company Hefti, SAPOGENAT 6-040 (HLB=8) by the company Hoechst, INTRASOL FA28/50/4 (HLB=8.1) by the company Stockhausen, SERDOX NOG 200 S (HLB=8.5) by the company Servo, BEROL 26 (HLB=8.9) by the company Berol Nobel, GENAPOL 0-050 (HLB=9) by the company Hoechst, PROX-ONIC LA-1/04 (HLB=9.2) by the company Protex, EUMULGIN O5 (HLB=9.5) by the company Henkel, ETOCAS 20 (HLB=9.6) by the company Croda, ANTAROX CO 520 (HLB=10) by the company Rhône-Poulenc, IMBENTIN POA/060 (HLB=10) by the company Kolb, TO-55-EL (HLB=10) by the company Hefti.

As examples of nonionic surfactants with an HLB less than or equal to 5, non-limiting mention may also be made of those sold under the following brand names:

SYNPERONIC PE L121 (HLB=0.5) by the company ICI PROX-ONIC EP 4060-1 (HLB=1) by the company Protex, SYNPERONIC PE L101 (HLB=1) by the company ICI, ETOCAS 29 (HLB=1.7) by the company Croda, GENAPOL PF 10 (HLB=2) by the company Hoechst, SYNPERONIC PE L81 (HLB=2) by the company ICI, PROX-ONIC EP 1090-1 (HLB=3) by the company Protex, SINNOPAL DPN2 (HLB=3.3) by the company Henkel, ANTAROX CA 210 (HLB=3.5) by the company Rhône-Poulenc, ANTAROX O1P (HLB=3.5) by the company Rhône-Poulenc, ALKASURF OP11 (HLB=3.6) by the company Rhône-Poulenc, TRITON X15 (HLB=3.6) by the company Rohm and Haas, ALKASURF OP1 (HLB=3.6) by the company Rhône-Poulenc, ARLACEL 121 (HLB=3.8) by the company ICI, PROX-ONIC HR or HRH-05 (HLB=3.8) by the company Protex, ETOCAS 5 (HLB=3.9) by the company Hoechst, GENAPOL PF20 (HLB=4) by the company Hoechst, IMBENTIN N/7 A (HLB=4) by the company Kolb, SYNPERONIC PE L122 (HLB=4) by the company ICI, ETHYLAN NP1 (HLB=4.5) by the company Harcros, IMBENTIN N/020 (HLB=4.5) by the company Kolb, KOTILEN O/3/020 (HLB=4.5) by the company Kolb, SYNPERONIC PE L31 (HLB=4.5) by the company ICI, TO-55-A (HLB=4.5) by the company Hefti, ALKASURF NP-1 (HLB=4.6) by the company Rhône-Poulenc, ANTAROX CO 210 (HLB=4.6) by the company Rhône-Poulenc, PROX-ONIC NP-1 (HLB=4.6) by the company Protex, RHODIASURF NP2 (HLB=4.6) by the company Rhône-Poulenc, SOPROPHOR BC2 (HLB=4.6) by the company Rhône-Poulenc, TRITON N17 (HLB=4.6) by the company Rohm and Haas, AKYPOROX NP15 (HLB=4.7) by the company Chem-y, TEXOFOR M2 (HLB=4.8) by the company Rhône-Poulenc, ALKASURF SA2 (HLB=4.9) by the company Rhône-Poulenc, ARLACEL 989 (HLB=4.9) by the company ICI, BRIJ 72 (HLB=4.9) by the company ICI, BRIJ 92 (HLB=4.9) by the company ICI, BRIJ 93 (HLB=4.9) by the company ICI, PROX-ONIC SA-1 or 2/02 (HLB=4.9) by the company Protex, SIMULSOL 72 (HLB=4.9) by the company SEPPIC, SIMULSOL 92 (HLB=4.9) by the company SEPPIC, VOLPO S-2 (HLB=4.9) by the company Croda, ARLACEL 581 (HLB=5.0) by the company ICI, ARLACEL 582 (HLB=5.0) by the company ICI, GENAPOL 0-020 (HLB=5.0) by the company Hoechst, IMBENTIN POA/020 (HLB=5.0) by the company Kolb, and MERGITAL Q2 (HLB=5.0) by the company Henkel.

For instance, a nonionic surfactant that is suitable for use as disclosed herein is hexadecyl alcohol comprising 2 mol of glycerol.

The at least one nonionic surfactant may be present in the composition in an amount ranging from 5% to 30% by weight, such as from 10% to 20% by weight, relative to the total weight of the dye composition.

The mesomorphic phase may also comprise at least one fatty alcohol comprising from 8 to 30 carbon atoms, for instance, from 12 to 22 carbon atoms. For example, the a at least one fatty alcohol may be hexadecanol.

The at least one fatty alcohol may be present in the composition in an amount ranging from 3% to 20% by weight, such as from 5% to 15% by weight, relative to the total weight of the dye composition.

As disclosed herein, the ammonia may be present in the dye composition in an amount ranging from 0.1% to 5% by weight, such as from 1% to 3% by weight relative to the total weight of the composition.

The oxidation dyes that may be used as disclosed herein are chosen from oxidation bases and couplers. For example, the compositions as disclosed herein may comprise at least one oxidation base.

The oxidation bases that may be used as disclosed herein may be chosen from those conventionally known in oxidation dyeing, and among which, non-limiting mention may be made of, for example, the ortho- and para-phenylenediamines, double bases, ortho- and para-aminophenols and heterocyclic bases as described below, and the acid addition salts.

Non-limiting examples of para-phenylenediamines that may be used include those of formula (I) and the acid addition salts thereof:

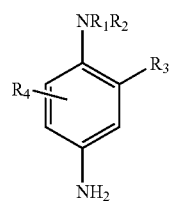

(I)

wherein:

$R_1$ is chosen from hydrogen, a $C_1$-$C_4$ alkyl group, a $C_1$-$C_4$ monohydroxyalkyl group, a $C_2$-$C_4$ polyhydroxyalkyl group, a ($C_1$-$C_4$)alkoxy($C_1$-$C_4$)alkyl group, a $C_1$-$C_4$ alkyl group substituted with a nitrogenous group, a phenyl group and a 4'-aminophenyl group;

$R_2$ is chosen from hydrogen, a $C_1$-$C_4$ alkyl group, a $C_1$-$C_4$ monohydroxyalkyl group, a $C_2$-$C_4$ polyhydroxyalkyl group, a ($C_1$-$C_4$)alkoxy($C_1$-$C_4$)alkyl group and a $C_1$-$C_4$ alkyl group substituted with a nitrogenous group;

wherein $R_1$ and $R_2$ may also form with the nitrogen atom that bears them a 5- or 6-membered nitrogenous heterocycle optionally substituted with at least one group chosen from alkyl, hydroxy and ureido groups;

$R_3$ is chosen from hydrogen, halogens, such as chlorine, a $C_1$-$C_4$ alkyl group, a sulfo group, a carboxy group, a $C_1$-$C_4$ monohydroxyalkyl group, a $C_1$-$C_4$ hydroxyalkoxy group, an acetylamino($C_1$-$C_4$)alkoxy group, a mesylamino($C_1$-$C_4$) alkoxy group and a carbamoylamino($C_1$-$C_4$)alkoxy group, and $R_4$ is chosen from hydrogen, halogens, and a $C_1$-$C_4$ alkyl group.

Among the nitrogenous groups of formula (I), non-limiting mention may be made, for example, of amino, mono($C_1$-$C_4$) alkylamino, di($C_1$-$C_4$)alkylamino, tri($C_1$-$C_4$)alkylamino, monohydroxy($C_1$-$C_4$)alkylamino, imidazolinium and ammonium radicals.

Non-limiting examples of para-phenylenediamines of formula (I) that may be mentioned include para-phenylenediamine; para-tolylenediamine; 2-chloro-para-phenylenediamine; 2,3-dimethyl-para-phenylenediamine; 2,6-dimethyl-para-phenylenediamine; 2,6-diethyl-para-phenylenediamine; 2,5-dimethyl-para-phenylenediamine; N,N-dimethyl-para-phenylenediamine; N,N-diethyl-para-phenylenediamine; N,N-dipropyl-para-phenylenediamine; 4-amino-N, N-diethyl-3-methylaniline; N,N-bis(β-hydroxyethyl)-para-phenylenediamine; 4-amino-N,N-bis(β-hydroxyethyl)-2-methylaniline; 4-amino-2-chloro-N, N-bis(β-hydroxyethyl)aniline; 2-β-hydroxyethyl-para-phenylenediamine; 2-fluoro-para-phenylenediamine; 2-isopropyl-para-phenylenediamine; N-(β-hydroxypropyl)-para-phenylenediamine; 2-hydroxymethyl-para-phenylenediamine; N,N-dimethyl-3-methyl-para-phenylenediamine; N,N-(ethyl-β-hydroxyethyl)-para-phenylenediamine; N-(β,γ-dihydroxypropyl)-para-phenylenediamine; N-(4'-aminophenyl)-para-phenylenediamine; N-phenyl-para-phenylenediamine; 2-β-hydroxyethyloxy-para-phenylenediamine; 2-β-acetylaminoethyloxy-para-phenylenediamine; N-(β-methoxyethyl)-para-phenylenediamine; 2-methyl-1-N-β-hydroxyethyl-para-phenylenediamine; and the acid addition salts thereof.

For instance, in one aspect of the present disclosure, the para-phenylenediamines of formula (I) may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the acid addition salts thereof.

As disclosed herein, the term "double bases" is understood to refer to compounds comprising at least two aromatic rings bearing amino and/or hydroxyl groups.

Among the double bases which can be used as oxidation bases in the dye compositions as disclosed herein, non-limiting mention may be made for example, of the compounds of formula (II), and the acid addition salts thereof:

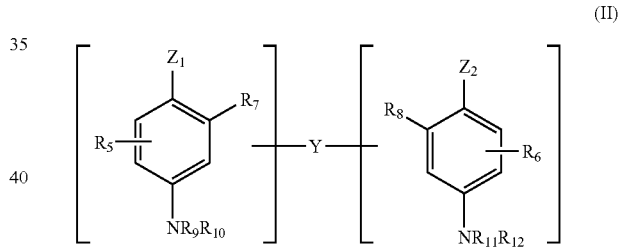

(II)

wherein:

$Z_1$ and $Z_2$, which may be identical or different, may be chosen from hydroxyl and —$NH_2$ groups which may be substituted with a $C_1$-$C_4$ alkyl group or with a linking element Y;

the linking element Y may be chosen from linear and branched alkylene chains comprising from 1 to 14 carbon atoms, and which may optionally comprise at least one nitrogenous groups and/or at least one hetero atom, such as oxygen, sulfur and nitrogen atoms, and optionally substituted with at least one group chosen from hydroxyl and $C_1$-$C_6$ alkoxy groups;

$R_5$ and $R_6$, which may be identical or different, can be chosen from hydrogen, halogens, a $C_1$-$C_4$ alkyl group, a $C_1$-$C_4$ monohydroxyalkyl group, a $C_2$-$C_4$ polyhydroxyalkyl group, a $C_1$-$C_4$ aminoalkyl group, and a linking element Y;

$R_7$, $R_8$, $R_9$, $R_{10}$, $R_{11}$ and $R_{12}$, which may be identical or different, are chosen from hydrogen, a linking element Y, and a $C_1$-$C_4$ alkyl group;

it being understood that the compounds of formula (II) comprise only one linking element Y per double base.

Among the nitrogenous groups of formula (II), non-limiting mention may be made of, for example, amino, mono($C_1$-

C₄)alkylamino, di(C₁-C₄)alkylamino, tri(C₁-C₄)alkylamino, monohydroxy(C₁-C₄)alkylamino, imidazolinium and ammonium groups.

Among the double bases of formula (II), non-limiting mention may be made of, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis-(ethyl)-N,N'-bis-(4'-amino-3'-methylphenyl)ethylenediamine and 1,8-bis(2,5-diaminophenoxy)-3,5-dioxoctane, and the acid addition salts thereof.

In another aspect of the present disclosure, the double bases of formula (II) can be chosen from N,N'-bis(β-hydroxyethyl)-N,N'-bis(4'-aminophenyl)-1,3-diaminopropanol and 1,8-bis(2,5-diaminophenoxy)-3,5-dioxaoctane, and the acid addition salts thereof.

In addition, non-limiting examples of para-aminophenols that may be used as disclosed herein include those of formula (III) and the acid addition salts thereof:

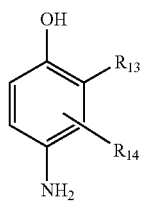

(III)

wherein:
R₁₃ is chosen from hydrogen, halogens, such as fluorine, C₁-C₄ alkyl, C₁-C₄ monohydroxyalkyl, (C₁-C₄)alkoxy(C₁-C₄)alkyl, C₁-C₄ aminoalkyl and hydroxy(C₁-C₄)alkylamino (C₁-C₄)alkyl groups, R₁₄ is chosen from hydrogen, halogens, such as fluorine, C₁-C₄ alkyl, C₁-C₄ monohydroxyalkyl, C₂-C₄ polyhydroxyalkyl, C₁-C₄ aminoalkyl, C₁-C₄ cyanoalkyl and (C₁-C₄) alkoxy-(C₁-C₄)alkyl groups.

Among the para-aminophenols of formula (III), non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the acid addition salts thereof.

In another aspect of the present disclosure, the ortho-aminophenols that may be used as oxidation bases as disclosed herein may be chosen from for example, 2-aminophenol, 2-amino-1-hydroxy-5-methylbenzene, 2-amino-1-hydroxy-6-methylbenzene and 5-acetamido-2-aminophenol, and the acid addition salts thereof.

Among the heterocyclic bases that can be used as oxidation bases in the dye compositions as disclosed herein, non-limiting mention may be made, for instance, of pyridine derivatives, pyrimidine derivatives, pyrazole derivatives, and the acid addition salts thereof.

Among the pyridine derivatives, non-limiting mention may be made of, for example, the compounds described, for example, in Patent Nos. GB 1,026,978 and GB 1,153,196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Among the pyrimidine derivatives, non-limiting mention may be made for instance, of the compounds described, for example, in German Patent DE 2 359 399, or Japanese Patent Nos. JP 88-169 571 and JP 91-10659, or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2, 750,048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl) amino]ethanol; 2-[(7-aminopyrazolo[1,5-a]pyrimidin-3-yl) (2-hydroxyethyl)amino]ethanol; 5,6-dimethylpyrazolo[1,5-a]pyrimidine-3,7-diamine; 2,6-dimethylpyrazolo[1,5-a] pyrimidine-3,7-diamine; 2,5,N7,N7-tetramethylpyrazolo[1, 5-a]pyrimidine-3,7-diamine and 3-amino-5-methyl-7-imidazolylpropylaminopyrazolo[1,5-a]pyrimidine, and the addition salts thereof, the tautomeric forms thereof, and when a tautomeric equilibrium exists, and the acid addition salts thereof.

Among the pyrazole derivatives, non-limiting mention may be made for example, of the compounds described in Patent Nos. DE 3 843 892, DE 4 133 957 and patent applications WO 94/08969, WO 94/08970, FR-A-2,733,749 and DE 195 43 988, such as 4,5-diamino-1-methylpyrazole; 3,4-diaminopyrazole; 4,5-diamino-1-(4'-chlorobenzyl)pyrazole; 4,5-diamino-1,3-dimethylpyrazole; 4,5-diamino-3-methyl-1-phenylpyrazole; 4,5-diamino-1-methyl-3-phenylpyrazole; 4-amino-1,3-dimethyl-5-hydrazinopyrazole; 1-benzyl-4,5-diamino-3-methylpyrazole; 4,5-diamino-3-tert-butyl-1-methylpyrazole; 4,5-diamino-1-tert-butyl-3-methylpyrazole; 4,5-diamino-1-(β-hydroxyethyl)-3-methylpyrazole; 4,5-diamino-1-(β-hydroxyethyl)pyrazole; 4,5-diamino-1-ethyl-3-methylpyrazole; 4,5-diamino-1-ethyl-3-(4'-methoxyphenyl) pyrazole; 4,5-diamino-1-ethyl-3-hydroxymethylpyrazole; 4,5-diamino-3-hydroxymethyl-1-methylpyrazole; 4,5-diamino-3-hydroxymethyl-1-isopropylpyrazole; 4,5-diamino-3-methyl-1-isopropylpyrazole; 4-amino-5-(2'-aminoethyl) amino-1,3-dimethylpyrazole; 3,4,5-triaminopyrazole; 1-methyl-3,4,5-triaminopyrazole; 3,5-diamino-1-methyl-4-methylaminopyrazole; and 3,5-diamino-4-(β-hydroxyethyl) amino-1-methylpyrazole; and the acid addition salts thereof.

As disclosed herein, the oxidation bases may be present in the composition in an amount ranging from 0.0005% to 12% by weight, relative to the total weight of the composition, such as ranging from 0.005% to 8% by weight, relative to the total weight of the composition.

The couplers that may be used in the dyeing composition as disclosed herein are those conventionally used in oxidation dye compositions, i.e., meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the acid addition salts thereof.

In one aspect of the present disclosure, the at least one coupler may be chosen from 2,4-diamino-1-(β-hydroxyethyloxy)benzene; 2-methyl-5-aminophenol; 5-N-(β-hydroxyethyl)amino-2-methylphenol; 3-aminophenol; 1,3-dihydroxybenzene; 1,3-dihydroxy-2-methylbenzene; 4-chloro-1,3-dihydroxybenzene; 2-amino-4-(β-hydroxyethylamino)-1-methoxybenzene; 1,3-diaminobenzene; 1,3-bis(2,4-diaminophenoxy)propane; sesamol; 1-amino-2-methoxy-4,5-methylenedioxybenzene; α-naphthol; 6-hydroxyindole; 4-hydroxyindole 4-hydroxy-N-methylindole; 6-hydroxyindoline; 2,6-dihydroxy-4-methylpyridine; 1-H-3-methyl pyrazol-5-one; 1-phenyl-3-methylpyrazol-5-one; 2-amino-3-hydroxypyridine; 3,6-dimethylpyrazolo[3,2-c]-1,2,4-triazole; and 2,6-dimethylpyrazolo[1,5-b]-1,2,4-triazole; and the acid addition salts thereof.

As disclosed herein, when present, the at least one coupler may be present, for example, in an amount ranging from 0.0001% to 10% by weight, relative to the total weight of the composition, such as ranging from 0.005% to 5% by weight, relative to the total weight of the composition.

In general, the acid addition salts of the oxidation bases and couplers can be chosen from, for example, hydrochlorides, hydrobromides, sulfates, tartrates, lactates and acetates.

In addition to the oxidation dyes defined above, the composition as disclosed herein may also comprise at least one direct dye, which may enrich the final shades with glints. For example, the at least one direct dye may be chosen from neutral, cationic and anionic nitro dyes, azo dyes and anthraquinone dyes. Further, the at least one direct dye may be present in the composition in an amount ranging from about 0.001% to 20%, such as from 0.01 to 10%, by weight, relative to the total weight of the composition.

The dye composition as disclosed herein may also comprise an effective amount of at least one adjuvant that are known in oxidation dyeing, for instance surfactants other than those described above, which are known in the art and may be chosen from anionic, cationic, nonionic, amphoteric and zwitterionic type; thickeners; fragrances; sequestering agents, such as EDTA and etidronic acid; UV-screen agents; waxes; silicones chosen from volatile and non-volatile, cyclic, linear and branched, organomodified (such as with amine groups) and non-organomodified silicones; preserving agents; ceramides; pseudoceramides; vegetable, mineral and synthetic oils; vitamins and provitamins, for instance panthenol, and opacifiers.

The composition as disclosed herein may also comprise at least one reducing agent and/or antioxidant. These may be chosen from, for example, sodium sulfite, thioglycolic acid, thiolactic acid, sodium bisulfite, dehydroascorbic acid, hydroquinone, 2-methylhydroquinone, tert-butylhydroquinone and homogentisic acid. The at least one reducing agent and/or antioxidant may be present in the composition in an amount ranging from about 0.05% to 1.5% by weight, relative to the total weight of the composition.

A person of ordinary skill in the art will take care to select the optional additional ingredient(s) described above, such that the advantageous properties intrinsically associated with the dye composition as disclosed herein are not, or are not substantially, adversely affected by the envisaged addition(s).

The aqueous medium that is suitable for dyeing comprises water and optionally at least one cosmetically acceptable organic solvent, for instance alcohols such as ethyl alcohol, isopropyl alcohol, benzyl alcohol and phenylethyl alcohol, or glycols or glycol ethers, for instance ethylene glycol monomethyl ether, monoethyl ether or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether. The optional at least one cosmetically acceptable solvent may be present in the composition in an amount ranging from about 0.5% to 20%, such as ranging from about 2% to 10% by weight, relative to the total weight of the composition.

In one aspect of the present disclosure the aqueous medium does not comprise an organic solvent.

Another aspect of the present disclosure is a process for preparing the dye composition as disclosed herein. The process comprises:

a) mixing at least one nonionic surfactant with an HLB value of less than or equal to 10, for example, ranging from 1 to 5, with water and optionally with one or more fatty alcohols, to prepare the mesomorphic phase, and b) adding at least one oxidation dye.

Ammonia may be added in step a) and/or in step b), in other words, it may be either added at the time of preparation of the mesomorphic phase, or it may already be present in the medium of the dye composition before addition of the mesomorphic phase, or may be added to the dye composition after incorporation of the mesomorphic phase.

Another aspect of the present disclosure is the incorporation of a mesomorphic phase comprising ammonia into a medium that itself comprises ammonia.

Another aspect of the present invention comprises a ready-to-use composition for the oxidation dyeing of keratin fibers, such as the hair, comprising, in a medium that is suitable for dyeing, at least one dye composition (A) as disclosed herein, and at least one composition (B) comprising at least one oxidizing agent.

For example, the mesomorphic phase may be present in the ready-to-use composition as disclosed herein, in an amount greater than or equal to 5% by weight, for instance, ranging from 10% to 30% by weight, relative to the total weight of the ready-to-use composition.

In the oxidizing composition (B), the at least one oxidizing agent may be chosen from, for instance, hydrogen peroxide, urea peroxide, alkali metal bromates and ferricyanides, and persalts such as perborates and persulfates. For example, the at least one oxidizing agent may be hydrogen peroxide. In one aspect of the present disclosure, the at least one oxidizing agent is chosen from an aqueous hydrogen peroxide solution with a titre ranging from about 1 to about 40 volumes, such as ranging from about 5 to about 40 volumes.

The at least one oxidizing agent may also be chosen from at least one redox enzymes such as laccases, peroxidases and 2-electron oxidoreductases (such as uricase), which may optionally be in the presence of the respective donor or co-factor thereof.

The oxidizing composition (B) may also comprise a mesomorphic phase.

The pH of the dye composition (A), or of the ready-to-use dye composition (i.e., the composition resulting from the mixing of the at least one dye composition (A) and the at least one oxidizing composition (B)) applied to the keratin fibers generally ranges from about 4 to about 12. For example, the pH may range from about 6 to about 11, and may be adjusted to the desired value using additional acidifying or basifying agents that are known in the art of dyeing of keratin fibers.

Non-limiting examples of additional basifying agents that may be mentioned include: alkali carbonates, alkanolamines such as monoethanolamine, diethanolamine and triethanolamine and derivatives thereof, oxyethylenated and/or oxypropylenated hydroxyalkylamines and ethylenediamines, sodium hydroxide, potassium hydroxide and the compounds of formula (IV):

wherein R is chosen from propylene residues optionally substituted with a group chosen from hydroxyl and $C_1$-$C_4$ alkyls; $R_{15}$, $R_{16}$, $R_{17}$ and $R_{18}$, which may be identical or different, are chosen from hydrogen, and $C_1$-$C_4$ alkyl and $C_1$-$C_4$ hydroxyalkyl groups.

The acidifying agents are conventionally, by way of example, mineral or organic acids, for instance hydrochloric acid, orthophosphoric acid, carboxylic acids, for instance tartaric acid, citric acid or lactic acid, or sulfonic acids.

The dyeing process as disclosed herein, may for example, comprise applying the ready-to-use composition as disclosed herein, prepared extemporaneously at the time of use, to wet or dry keratin fibers, and leaving the composition on the fibers to act for a leave-in time, for example, ranging from 1 to 60 minutes approximately, such as from 10 to 45 minutes approximately, rinsing the fibers and then optionally washing them with shampoo, then rinsing them again and drying them.

The present disclosure also relates to a multi-compartment device or kit for the oxidation dyeing of keratin fibers, for example the hair, comprising at least two compartments, wherein at least one compartment contains at least one dye composition (A), as defined above and at least one compartment contains at least one oxidizing composition (B), as defined above.

The examples that follow are given as illustrations of the present disclosure.

EXAMPLE 1

Preparation of a Lamellar Mesomorphic Phase $L_\beta$

Water and ammonia were added to a mixture of hexadecyl alcohol comprising 2 mol of glycerol ($C_{16}G_2$) and hexadecanol ($C_{16}OH$), in the proportions indicated in Table 1 below. The dispersion was subjected to three 2-hour heating cycles, wherein each cycle varied the temperature from room temperature to a temperature of about 70° C., with stirring.

An aqueous composition was also prepared to serve as a control, as was a dispersion of the lamellar phase $L_\beta$ in water (or dispersion $L_\beta$).

TABLE 1

|  | Weight % | | | |
| --- | --- | --- | --- | --- |
|  | $C_{16}G_2$ | $C_{16}OH$ | $NH_3$ | Water |
| Aqueous composition | — | — | 1 | 99 |
| Lamellar phase $L_\beta$ | 52.5 | 32.5 | 1 | 14 |
| Dispersion $L_\beta$ | 10.5 | 6.5 | 1 | 82 |

The structure of the lamellar phase was checked by polarization microscopy and small-angle X-ray diffusion. The release of ammonia was then measured with colorimetric tubes, on samples of 10 ml of each of the compositions, contained in 30 ml open flasks. The resulting uncertainty of the results is at most about 10%. The measurements for each sample lasted 20 to 30 seconds.

|  | Release of $NH_3$ (ppm) after | | | |
| --- | --- | --- | --- | --- |
|  | 1 min. | 5 min. | 10 min. | 20 min. |
| Aqueous composition | >1400 | 1367 | 1300 | 1133 |
| Lamellar phase $L_\beta$ | 433 | 283 | 183 | 133 |
| Dispersion $L_\beta$ | 533 | 333 | 367 | 350 |

The sample of lamellar phase diffused from 3 to 8 times less than the control sample.

The dispersion of the lamellar phase in excess water presented a release that was 3 to 4 times less than that of the control sample. This result was found whether the ammonia was present in the mesomorphic phase before dispersion or in the dispersion water.

EXAMPLE 2

A dye composition according to the present disclosure was prepared by mixing, at room temperature (about 20-25° C.), 100 g. of the lamellar phase as prepared in Example 1, and 30 g. of a dye medium, the components thereof being indicated below.

The components of the dye composition, including the components of the lamellar phase, are indicated below with weight proportions thereof relative to the total weight of the dye composition.

| Components of the dye composition: | Weight % |
| --- | --- |
| Oleic acid | 2.1 |
| 1-methyl-2,5-diaminobenzene | 0.31 |
| Pentasodium salt of diethylenetriamine-pentacetic acid in 40% aqueous solution | 1.5 |
| Cetylstearyl alcohol | 12.5 |
| Ammonium thiolactate in 58% aqueous solution | 0.62 |
| Tetramethyl-hexamethylenediamine/1,3-dichloropropylene polycondensate in 60% aqueous solution | 3.9 |
| 1,3-bis[(4-aminophenyl)(2-hydroxyethyl)amino]-2-propanol tetrahydrochloride | 0.04 |
| 1,3-dihydroxybenzene | 0.001 |
| 1-hydroxy-4-aminobenzene | 0.08 |
| Oxyethylenated (30 EO) oleocetyl alcohol | 2.8 |
| Monoethanolamine | 0.49 |
| Oleic alcohol | 2.1 |
| 1-methyl-2-hydroxy-4-aminobenzene | 0.62 |
| 1-methyl-2-hydroxy-4-beta-hydroxyethylaminobenzene | 0.15 |
| Ammonia (20%) | 12.0 |
| Hexadecyl alcohol containing 2 moles of glycerol | 12.1 |
| Hexadecanol | 7.5 |
| Deionized water | qs 100 |

A significant reduction of the ammonia release was observed over time.

What is claimed is:

1. A dye composition comprising, in an aqueous medium suitable for dyeing, at least one oxidation dye, ammonia, and at least one mesomorphic phase present in an amount greater than or equal to 10% by weight, relative to the total weight of the dye composition, the at least one mesomorphic phase comprising at least one nonionic surfactant with an HLB value of less than or equal to 10 in an amount ranging from 10% to 20%, relative to the weight of the dye composition, the at least one mesomorphic phase chosen from inverse hexagonal phases ($H_2$), lamellar phases ($L_\beta$) and inverse cubic phases ($I_2$ and $V_2$).

2. The dye composition according to claim 1, wherein the at least one mesomorphic phase is present in an amount greater than or equal to 15% by weight, relative to the total weight of the dye composition.

3. The dye composition according to claim 1, wherein the at least one mesomorphic phase is present in an amount ranging from 10% to 85% by weight, relative to the total weight of the dye composition.

4. The dye composition according to claim 1, wherein the at least one mesomorphic phase is chosen from a lamellar phase $L_\beta$.

5. The dye composition according to claim 1, wherein the at least one mesomorphic phase comprises at least one nonionic surfactant with an HLB value ranging from 1 to 5.

6. The dye composition according to claim 1, wherein the at least one non ionic surfactant is chosen from polyglycerolated fatty alcohols, monooxyethylenated or polyoxyethylenated fatty alcohols, monoglycerolated or polyglycerolated fatty amides comprising from 1 to 5 glycerol groups, monooxyethylenated or polyoxyethylenated alkylphenols comprising greater than or equal to 2 mol of ethylene oxide, condensates of ethylene oxide and of propylene oxide with fatty alcohols, polyoxyethylenated vegetable oils comprising more than 5 mol of ethylene oxide, fatty acid esters of polyethylene glycols, and polyoxyethylenated fatty acid esters of sorbitol.

7. The dye composition according to claim 6, wherein the nonionic surfactant is hexadecyl alcohol comprising 2 mol of glycerol.

8. The dye composition according to claim 1, wherein the at least one mesomorphic phase further comprises at least one fatty alcohol comprising from 8 to 30 carbon atoms.

9. The dye composition according to claim 8, wherein the at least one fatty alcohol is hexadecanol.

10. The dye composition according to claim 8, wherein the at least one fatty alcohol is present in the composition in an amount ranging from 3% to 20% by weight, relative to the total weight of the dye composition.

11. The dye composition according to claim 10, wherein the at least one fatty alcohol is present in the composition in an amount ranging from 5% to 15% by weight, relative to the total weight of the dye composition.

12. The dye composition according to claim 1, wherein the ammonia is present in the composition in an amount ranging from 0.1% to 5% by weight, relative to the total weight of the dye composition.

13. The dye composition according to claim 12, the ammonia is present in the composition in an amount ranging from 1% to 3% by weight, relative to the total weight of the dye composition.

14. The dye composition according to claim 1, wherein the at least one oxidation dye is chosen from oxidation bases and couplers.

15. The dye composition according to claim 14, wherein the oxidation dye is chosen from at least one oxidation base.

16. The dye composition according to claim 15, wherein the at least one oxidation base is chosen from ortho- and para-phenylenediamines, double bases, ortho- and para-aminophenols and heterocyclic bases, and the acid addition salts thereof.

17. The dye composition according to claim 16, wherein the para-phenylenediamines are chosen from the compounds of formula (I):

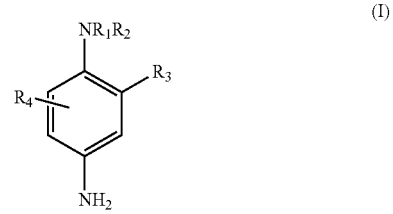

wherein:

$R_1$ is chosen from hydrogen, a $C_1$-$C_4$ alkyl group, a $C_1$-$C_4$ monohydroxyalkyl group, a $C_2$-$C_4$ polyhydroxyalkyl group, a ($C_1$-$C_4$)alkoxy($C_1$-$C_4$)alkyl group, a $C_1$-$C_4$ alkyl group substituted with a nitrogenous group, a phenyl group, and a 4'-aminophenyl group;

$R_2$ is chosen from hydrogen, a $C_1$-$C_4$ alkyl group, a $C_1$-$C_4$ monohydroxyalkyl group, a $C_2$-$C_4$ polyhydroxyalkyl group, a ($C_1$-$C_4$)alkoxy($C_1$-$C_4$)alkyl group and a $C_1$-$C_4$ alkyl group substituted with a nitrogenous group;

wherein $R_1$ and $R_2$ may also form, with the nitrogen atom that bears them, a 5- or 6-membered nitrogenous heterocycle optionally substituted with at least one group chosen from alkyl, hydroxy and ureido groups;

$R_3$ is chosen from hydrogen, halogens, a $C_1$-$C_4$ alkyl group, a sulfo group, a carboxy group, a $C_1$-$C_4$ monohydroxyalkyl group, a $C_1$-$C_4$ hydroxyalkoxy group, an acetylamino($C_1$-$C_4$)alkoxy group, a mesylamino($C_1$-$C_4$)alkoxy group and a carbamoylamino($C_1$-$C_4$)alkoxy group, $R_4$ is chosen from hydrogen, halogens, and $C_1$-$C_4$ alkyl groups.

18. The dye composition according to claim 17, wherein the nitrogenous groups are chosen from amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium groups.

19. The dye composition according to claim 17, wherein the halogens are chosen from chlorine.

20. The dye composition according to claim 16, wherein the double bases are chosen from the compounds of formula (II):

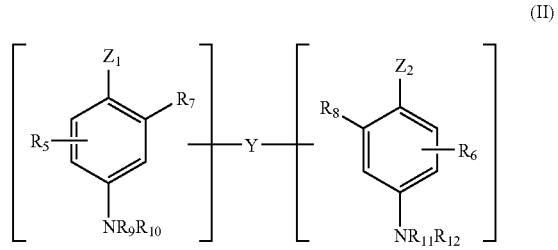

wherein, $Z_1$ and $Z_2$, which may be identical or different, are chosen from hydroxyl and —$NH_2$ groups that may be substituted with a $C_1$-$C_4$ alkyl group or with a linking element Y;

the linking element Y is chosen from linear and branched alkylene chains comprising from 1 to 14 carbon atoms, which may be interrupted by or terminated by at least one nitrogenous group and/or at least one hetero atom, and optionally substituted with at least one group chosen from hydroxyl and $C_1$-$C_6$ alkoxy groups;

$R_5$ and $R_6$, which may be identical or different, are chosen from hydrogen, halogens, a $C_1$-$C_4$ alkyl group, a $C_1$-$C_4$ monohydroxyalkyl group, a $C_2$-$C_4$ polyhydroxyalkyl group, a $C_1$-$C_4$ aminoalkyl group, and a linking element Y;

$R_7$, $R_8$, $R_9$, $R_{10}$, $R_{11}$ and $R_{12}$, which may be identical or different, are chosen from hydrogen, a linking element Y, and $C_1$-$C_4$ alkyl groups;

with the proviso that the compounds of formula (II) comprise only one linking element Y per double base.

21. The dye composition according to claim 20, wherein the at least one hetero atom is chosen from oxygen, sulfur and nitrogen atoms.

22. The dye composition according to claim 20, wherein the nitrogenous groups are chosen from amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium groups.

23. The dye composition according to claim 16, wherein the para-aminophenols are chosen from the compounds of formula (III):

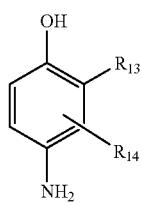

(III)

wherein:

$R_{13}$ is chosen from hydrogen, halogens, $C_1$-$C_4$ alkyl, $C_1$-$C_4$ monohydroxyalkyl, ($C_1$-$C_4$)alkoxy($C_1$-$C_4$)alkyl, $C_1$-$C_4$ aminoalkyl and hydroxy($C_1$-$C_4$)alkylamino($C_1$-$C_4$) alkyl groups, $R_{14}$ is chosen from hydrogen, halogens, $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl and ($C_1$-$C_4$)alkoxy-($C_1$-$C_4$)alkyl groups.

24. The dye composition according to claim 23, wherein the halogens are chosen from fluorine.

25. The dye composition according to claim 16, wherein the heterocyclic bases are chosen from pyridine derivatives, pyrimidine derivatives, and pyrazole derivatives.

26. The dye composition according to claim 25, wherein the pyrimidine derivatives are chosen from pyrazolopyrimidines.

27. The dye composition according to claim 15, wherein the at least one oxidation base is present in the composition in an amount ranging from 0.0005% to 12% by weight, relative to the total weight of the dye composition.

28. The dye composition according to claim 14, wherein the at least one coupler is chosen from meta-phenylenediamines, meta-aminophenols, meta-diphenols and heterocyclic couplers, and the acid addition salts thereof.

29. The dye composition according to claim 14, wherein the at least one coupler is present in the composition in an amount ranging from 0.0001% to 10% by weight, relative to the total weight of the composition.

30. The dye composition according to claim 16, wherein the acid addition salts of the at least one oxidation base are chosen from hydrochlorides, hydrobromides, sulfates, tartrates, lactates and acetates.

31. The dye composition according to claim 28, wherein the acid addition salts of the at least one coupler are chosen from hydrochlorides, hydrobromides, sulfates, tartrates, lactates and acetates.

32. The dye composition according to claim 1, further comprising at least one direct dye.

33. The dye composition according to claim 1, further comprising at least one adjuvants chosen from anionic, cationic, amphoteric, zwitterionic and nonionic surfactants, provided that the nonionic surfactants are those other than nonionic surfactants with an HLB value of less than or equal to 10; thickeners; fragrances; sequestering agents; UV-screening agents; waxes; silicones chosen from volatile and non-volatile, cyclic, linear and branched, organomodified and non-organomodified silicones; preserving agents; ceramides; pseudoceramides; vegetable, mineral and synthetic oils; vitamins and provitamins; opacifiers; reducing agents; and antioxidants.

34. The dye composition according to claim 1, wherein the cosmetically acceptable aqueous medium comprises water, and may optionally comprise cosmetically acceptable organic solvents.

35. A process for preparing a dye composition comprising:
a) preparing at least one mesomorphic phase by mixing at least one nonionic surfactant with an HLB value of less than or equal to 10 in an amount ranging from 10% to 20% by weight, relative to the weight of the dye composition, with water and optionally with at least one fatty alcohol, the at least one mesomorphic phase chosen from inverse hexagonal phases ($H_2$), lamellar phases ($L_\beta$) and inverse cubic phases ($I_2$ and $V_2$), and
b) adding at least one oxidation dye to the at least one mesomorphic phase,
wherein ammonia is added in step a), step b), or both.

36. The process according to claim 35, wherein the at least one non ionic surfactant of step a) has an HLB value ranging from 1 to 5.

37. A ready-to-use composition for the oxidation dyeing of keratin fibers, comprising, in a medium suitable for dyeing, at least one dye composition (A) comprising at least one oxidation dye, ammonia, and at least one mesomorphic phase present in composition (A) in an amount greater than or equal to 10% by weight, relative to the weight of composition (A), the at least one mesomorphic phase comprising at least one nonionic surfactant with an HLB value of less than or equal to 10 in an amount ranging from 10% to 20% by weight, relative to the weight of composition (A), and at least one composition (B) comprising at least one oxidizing agent, the at least one mesomorphic phase chosen from inverse hexagonal phases ($H_2$), lamellar phases ($L_\beta$) and inverse cubic phases ($I_2$ and $V_2$).

38. The ready-to-use composition according to claim 37, wherein the mesomorphic phase is present in the ready-to-use composition in an amount greater than or equal to 5% by weight, relative to the total weight of the ready-to-use composition.

39. The ready-to-use composition according to claim 38, wherein mesomorphic phase is present in the ready-to-use composition in an amount ranging from 10% to 30% by weight, relative to the total weight of the ready-to-use composition.

40. The ready-to-use composition according to claim 37, wherein the at least one oxidizing agent is chosen from hydrogen peroxide, urea peroxide, alkali metal bromates and ferricyanides, persalts, and redox enzymes, optionally in the presence of the respective donor or co-factor thereof.

41. The ready-to-use composition according to claim 40, wherein the redox enzymes are chosen from laccases, peroxidases, and 2-electron oxidoreductases.

42. The ready-to-use composition according to claim 40, wherein the at least one oxidizing agent is hydrogen peroxide.

43. The ready-to-use composition according to claim 41, wherein the at least one oxidizing agent is an aqueous hydrogen peroxide solution with a titre ranging from 1 to 40 volumes.

44. The ready-to-use composition according to claim 37, wherein the ready-to-use composition has a pH ranging approximately from 4 to 12.

45. An oxidizing composition, comprising at least one oxidizing agent chosen from hydrogen peroxide, urea peroxide, alkali metal bromates and ferricyanides, persalts, and redox enzymes, optionally in the presence of the respective donor or co-factor thereof, and at least one mesomorphic phase chosen from inverse hexagonal phases ($H_2$), lamellar phases ($L_\beta$) and inverse cubic phases ($I_2$ and $V_2$), wherein the at least one mesomorphic phase is present in the oxidizing composition in an amount greater than or equal to 10% by weight, relative to the total weight of the oxidizing composition, the at least one mesomorphic phase comprising at least one nonionic surfactant with an HLB value of less than or equal to 10 in an amount ranging from 10% to 20% by weight, relative to the weight of the dye composition.

46. A method for dyeing keratin fibers, comprising applying to wet or dry keratin fibers, a ready-to-use composition comprising, in a medium suitable for dyeing, at least one composition (A) comprising at least one oxidation dye, ammonia, and at least one mesomorphic phase present in composition (A) in an amount greater than or equal to 10% by weight, relative to the total weight of composition (A), the at least one mesomorphic phase comprising at least one nonionic surfactant with an HLB value of less than or equal to 10 in an amount ranging from 10% to 20% by weight, relative to the weight of composition (A), the at least one mesomorphic phase chosen from inverse hexagonal phases ($H_2$), lamellar phases ($L_\beta$) and inverse cubic phases ($I_2$ and $V_2$), and at least one composition (B) comprising at least one oxidizing agent, wherein the ready-to-use composition is prepared extemporaneously at the time of use, and wherein the ready-to-use composition is left on the keratin fibers to act for a leave-in time ranging from 1 to 60 minutes approximately, rinsing the fibers and then optionally washing them with shampoo, then rinsing them again and drying them.

47. The method according to claim 45, wherein the leave-in time ranges approximately from 10 to 45 minutes.

48. A multi-compartment kit for the oxidation dyeing of keratin fibers, comprising at least two compartments, wherein at least one compartment contains at least one dye composition comprising at least one oxidation dye, ammonia, and at least one mesomorphic phase present in the dye composition in an amount greater than or equal to 10% by weight, relative to the total weight of the dye composition, the at least one mesomorphic phase comprising at least one nonionic surfactant with an HLB value of less than or equal to 10 in an amount ranging from 10% to 20% by weight, relative to the weight of the dye composition, the at least one mesomorphic phase chosen from inverse hexagonal phases ($H_2$), lamellar phases ($L_\beta$) and inverse cubic phases ($I_2$ and $V_2$), and at least one other compartment contains a composition comprising at least one oxidizing agent.

* * * * *